United States Patent
Bishop

(10) Patent No.: US 12,061,138 B2
(45) Date of Patent: Aug. 13, 2024

(54) APPARATUS WITH HETEROGENEOUS PROCESSING MODULES

(71) Applicant: Cepheid, Sunnyvale, CA (US)

(72) Inventor: John L. Bishop, Sunnyvale, CA (US)

(73) Assignee: Cepheid, Sunnyvale, CA (US)

( * ) Notice: Subject to any disclaimer, the term of this patent is extended or adjusted under 35 U.S.C. 154(b) by 389 days.

(21) Appl. No.: 16/155,723

(22) Filed: Oct. 9, 2018

(65) Prior Publication Data

US 2019/0041300 A1 Feb. 7, 2019

Related U.S. Application Data

(62) Division of application No. 14/396,035, filed as application No. PCT/US2013/038210 on Apr. 25, 2013, now Pat. No. 10,132,728.

(60) Provisional application No. 61/639,820, filed on Apr. 27, 2012.

(51) Int. Cl.
| | |
|---|---|
| *G01N 1/31* | (2006.01) |
| *C12Q 1/6806* | (2018.01) |
| *C12Q 1/6876* | (2018.01) |
| *G01N 33/68* | (2006.01) |
| *G01N 35/00* | (2006.01) |

(52) U.S. Cl.
CPC ............ *G01N 1/31* (2013.01); *C12Q 1/6806* (2013.01); *C12Q 1/6876* (2013.01); *G01N 33/6845* (2013.01); *G01N 35/00* (2013.01); *G01N 35/00871* (2013.01); *C12Q 2600/16* (2013.01)

(58) Field of Classification Search
None
See application file for complete search history.

(56) References Cited

U.S. PATENT DOCUMENTS

| | | |
|---|---|---|
| 4,169,125 A | 9/1979 | Rodriguez |
| 5,856,174 A | 1/1999 | Lipshutz |
| 5,928,952 A | 7/1999 | Hutchins |
| 6,066,243 A | 5/2000 | Anderson |

(Continued)

FOREIGN PATENT DOCUMENTS

| | | |
|---|---|---|
| EP | 1612561 A1 | 1/2006 |
| EP | 1305638 B1 | 12/2010 |

(Continued)

OTHER PUBLICATIONS

Batzer, Mark A. et al., "Enhanced evolutionary PCR using oligonucleotides with inosine at the 3'-terminus," Nucleic Acids Research, 1991, vol. 19, No. 18, p. 5081.

(Continued)

*Primary Examiner* — Robert T. Crow
(74) *Attorney, Agent, or Firm* — Kilpatrick Townsend & Stockton LLP

(57) ABSTRACT

A biological sample processing apparatus having an enclosure. A plurality of sample processing modules are held by the enclosure. Each sample processing module is configured to hold a removable sample cartridge and to only perform sample processing on a sample within the corresponding removable sample cartridge. Each sample processing module is configured to perform at least one of a plurality of testing processes on the sample within the removable sample cartridge. At least one module in the apparatus is configured to perform nucleic acid amplification and detection.

10 Claims, 10 Drawing Sheets

(56) References Cited

U.S. PATENT DOCUMENTS

| | | |
|---|---|---|
| 6,168,948 B1 | 1/2001 | Anderson |
| 6,391,541 B1 | 5/2002 | Petersen |
| 6,586,176 B1 | 7/2003 | Trnovsky et al. |
| 6,660,228 B1 | 12/2003 | Chang |
| 6,739,531 B2 | 5/2004 | Taylor |
| 6,776,961 B2 | 8/2004 | Lindsey |
| 2002/0042125 A1 | 4/2002 | Peterson |
| 2002/0177135 A1 | 11/2002 | Doung |
| 2004/0157336 A1* | 8/2004 | Petroff .................. B01L 9/527 422/65 |
| 2008/0153096 A1 | 6/2008 | Witty |
| 2008/0200343 A1 | 8/2008 | Clemens |
| 2009/0041626 A1 | 2/2009 | Atkin |
| 2009/0130745 A1* | 5/2009 | Williams ................. B01L 7/52 435/287.2 |
| 2009/0227006 A1* | 9/2009 | Kopp ................. G01N 35/0099 435/287.2 |
| 2009/0305392 A1* | 12/2009 | Alfredsson ...... G01N 35/00712 435/286.1 |
| 2010/0048899 A1 | 2/2010 | Dandala et al. |
| 2010/0129827 A1 | 5/2010 | Mcmillan |
| 2010/0261179 A1* | 10/2010 | Betley .................... B03C 1/288 210/222 |
| 2011/0091357 A1 | 4/2011 | Blatt |
| 2013/0079236 A1 | 3/2013 | Holmes |

FOREIGN PATENT DOCUMENTS

| | | |
|---|---|---|
| GB | 1561042 A | 2/1980 |
| JP | 2001-527220 A | 12/2001 |
| JP | 2005-261298 | 9/2005 |
| JP | 2007-187677 | 7/2007 |
| WO | 00/72970 A1 | 12/2000 |
| WO | 00/73412 A2 | 12/2000 |
| WO | 02/18902 A1 | 3/2002 |
| WO | 2008/012104 A2 | 1/2008 |
| WO | 2011/067559 A1 | 6/2011 |
| WO | 2012/012779 A2 | 1/2012 |

OTHER PUBLICATIONS

Innis, Michael A. et al. (eds.), PCR Protocols: A Guide to Methods and Applications, 1990, Academic Press, Inc., NY, USA.

Ohtsuka, Eiko et al., "An Alternative Approach to Deoxyoligonucleotides as Hybridization Probes by Insertion of Deoxyinosine at Ambiguous Codon Positions," Journals of Biological Chemistry, Mar. 10, 1985, vol. 260, issue 5, pp. 2605-2608.

Raja et al., "Technology for Automated, Rapid, and Quantitative PCR or Reverse Transcription—PCR Clinical Testing," *Clinical Chemistry*, 51:5 (2005) 882-890.

International Search Report and Written Opinion mailed Aug. 14, 2013, from PCT Application No. PCT/US2013/038210 (12 pages).

International Preliminary Report on Patentability mailed Nov. 6, 2014, from PCT Application No. PCT/US2013/038210 (8 pages).

\* cited by examiner

APPARATUS WITH HETEROGENEOUS PROCESSING MODULES

This application is a Divisional of U.S. application Ser. No. 14/396,035, filed Oct. 21, 2014, which is a U.S. National Phase of International Application No. PCT/US2013/038210, filed Apr. 25, 2013, which claims priority to U.S. Provisional Patent Application No. 61/639,820, filed on Apr. 27, 2012, the disclosures of which are incorporated by reference.

BACKGROUND OF THE INVENTION

The analysis of samples such as clinical or environmental samples generally involves a series of processing steps, which may include separate chemical, optical, electrical, mechanical, thermal, or acoustical processing of the samples. Conventional systems for processing samples are each typically dedicated to one type of assay. This is because each type of assay is very different with respect to target attributes being measured, and also has a specific series of pre- and post-testing steps.

Because different assays require different configurations, conventional systems are not versatile nor easily adaptable to different protocols. Accordingly, systems for performing assays are as different as the assays themselves. There is an unanswered need to condense these systems in a manner that remains flexible for the present and future needs of a user.

BRIEF SUMMARY OF THE INVENTION

Some embodiments of the invention relate to a biological sample processing apparatus having an enclosure. A plurality of sample processing modules can be held by the enclosure. Each sample processing module is configured to hold a removable sample cartridge and to only perform sample processing on a sample within the corresponding removable sample cartridge. Each sample processing module can be configured to perform at least one of a plurality of testing processes on the sample within the removable sample cartridge. At least one module in the apparatus can be configured to perform nucleic acid amplification and detection. At least one module in the apparatus can be a sample preparation module configured to only perform sample preparation. At least one module in the apparatus can be configured to perform immunoassays for protein detection.

In some embodiments, at least one sample processing module can be configured for hybridizing a nucleic acid to an array on a solid support.

In some embodiments at least one sample processing module can be configured for nucleic acid amplication and detection in a multiplex array of wells, wherein each separate well comprises a separate nucleic acid amplification reaction. In some embodiments, each of the separate wells of the multiplex array of wells is capable of carrying out a multiplex reaction (e.g. nested PCR).

In some embodiments, the at least one sample preparation module can be configured to prepare a sample to undergo a sample processing protocol for at least one nucleic acid.

In some embodiments, at least one sample processing module can be configured for detection of at least one protein analyte.

In some embodiments, at least one sample processing module can be configured for assessing a chromosomal copy number of at least one gene of interest.

In some embodiments, at least one sample processing module can be configured for performing a multiplex detection of at least two nucleic acid analytes.

In some embodiments, at least one sample processing module can be configured for performing a multiplex detection of at least two protein analytes.

In some embodiments, at least one sample processing module can be configured for sequencing and detecting a nucleic acid molecule.

In some embodiments, the plurality of sample processing modules can include at least one module for detecting at least one protein analyte contained within a biological sample within a test cartridge, at least one module for assessing chromosomal copy number of at least one gene of interest contained within a biological sample within a test cartridge; and at least one module for performing a sample processing protocol for at least one nucleic acid contained within a biological sample within a test cartridge.

In some embodiments, the enclosure can hold at least two sample processing modules.

In some embodiments, the plurality of sample processing modules includes different modules configured for different types of sample processing.

In some embodiments, the plurality of sample processing modules can include at least one module that can be configured for hybridizing a nucleic acid to an array on a solid support and/or at least one module that can be configured for detection of at least one protein analyte and/or at least one module that can be configured for assessing a chromosomal copy number of at least one gene of interest and/or at least one module that can be configured for performing a multiplex detection of at least two nucleic acid analytes and/or at least one module that can be configured for performing a multiplex detection of at least two nucleic acid analytes and/or at least one module that can be configured for performing a multiplex detection of at least two protein analytes and/or at least one module that can be configured for sequencing and detecting a nucleic acid molecule and/or at least one module that can be configured for performing PCR and/or at least one sample processing module that can be configured for performing rapid PCR.

In some embodiments, the plurality of sample processing modules can be up to 16 sample processing modules made up of a combination of modules, which in some embodiments are different types of modules, such as 1, 2, 3, 4, 5, 6, 7, 8, 9, 10, 11, 12, 13, 14, or 15 modules (depending on whether other types of modules are included within the plurality) that can be configured for a first type of assay and 1, 2, 3, 4, 5, 6, 7, 8, 9, 10, 11, 12, 13, 14, or 15 modules (depending on whether other types of modules are included within the plurality) that can be configured for a second type of assay and/or 1, 2, 3, 4, 5, 6, 7, 8, 9, 10, 11, 12, 13, 14, or 15 modules (depending on whether other types of modules are included within the plurality) that can be configured for a third type of assay and/or 1, 2, 3, 4, 5, 6, 7, 8, 9, 10, 11, 12, 13, 14, or 15 modules (depending on whether other types of modules are included within the plurality) that can be configured for a fourth type of assay and/or 1, 2, 3, 4, 5, 6, 7, 8, 9, 10, 11, 12, 13, 14, or 15 modules (depending on whether other types of modules are included within the plurality) that can be configured for a fifth type of assay and/or 1, 2, 3, 4, 5, 6, 7, 8, 9, 10, 11, 12, 13, 14, or 15 modules (depending on whether other types of modules are included within the plurality) that can be configured for a sixth type of assay and/or 1, 2, 3, 4, 5, 6, 7, 8, 9, 10, 11, 12, 13, 14, or 15 modules (depending on whether other types of modules are included within the plurality) that can be configured for a seventh type of assay and/or 1, 2, 3, 4, 5, 6, 7, 8, 9, 10, 11, 12, 13, 14, or 15 modules (depending on whether other types of modules are included within the plurality) that can be configured for an eighth type of assay and/or 1, 2, 3, 4, 5, 6, 7, 8, 9, 10, 11, 12, 13, 14, or 15 modules (depending on whether other types of modules are included within the plurality) that can be configured for a ninth type of assay and/or 1, 2, 3, 4, 5, 6, 7, 8, 9, 10, 11, 12, 13, 14, or 15 modules (depending on whether other types of modules are included within the plurality) that can be configured for a tenth type of assay and/or 1, 2, 3, 4, 5, 6, 7, 8, 9, 10, 11, 12, 13, 14, or 15 modules (depending on whether other types of modules are included within the plurality) that can be configured for an eleventh type of assay and/or 1, 2, 3, 4, 5, 6, 7, 8, 9, 10, 11, 12, 13, 14, or 15 modules (depending on whether other types of modules are included within the plurality) that can be configured for a twelfth type of assay and/or 1, 2, 3, 4, 5, 6, 7, 8, 9, 10, 11, 12, 13, 14, or 15 modules (depending on whether other types of modules are included within the plurality) that can be configured for a thirteenth type of assay and/or 1, 2, 3, 4, 5, 6, 7, 8, 9, 10, 11, 12, 13, 14, or 15 modules (depending on whether other types of modules are included within the plurality) that can be configured for a fourteenth type of assay and/or 1, 2, 3, 4, 5, 6, 7, 8, 9, 10, 11, 12, 13, 14, or 15 modules (depending on whether other types of modules are included within the plurality) that can be configured for a fifteenth type of assay.

In some embodiments, the plurality of sample processing modules can be up to 16 sample processing modules made up of at lest one module configured to perform nucleic acid amplification and detection and a combination of modules, which in some embodiments are different types of modules, such as 1, 2, 3, 4, 5, 6, 7, 8, 9, 10, 11, 12, 13, 14, or 15 modules (depending on whether other types of modules are included within the plurality) that can be configured for hybridizing a nucleic acid to an array on a solid support and/or 1, 2, 3, 4, 5, 6, 7, 8, 9, 10, 11, 12, 13, 14, or 15 modules (depending on whether other types of modules are included within the plurality) that can be configured for detection of at least one protein analyte and/or 1, 2, 3, 4, 5, 6, 7, 8, 9, 10, 11, 12, 13, 14, or 15 modules (depending on whether if other types of modules are included within the plurality) that can be configured for assessing a chromosomal nucleic acid copy number of at least one nucleic acid and/or 1, 2, 3, 4, 5, 6, 7, 8, 9, 10, 11, 12, 13, 14, or 15 modules (depending on whether if other types of modules are included within the plurality) that can be configured for performing a multiplex detection of at least two nucleic acid analytes and/or 1, 2, 3, 4, 5, 6, 7, 8, 9, 10, 11, 12, 13, 14, or 15 modules (depending on whether other types of modules are included within the plurality) that can be configured for performing a nucleic acid amplification and detection in a multiplex array of wells, wherein each separate well comprises a separate nucleic acid amplification reaction and/or 1, 2, 3, 4, 5, 6, 7, 8, 9, 10, 11, 12, 13, 14, or 15 modules (depending on whether other types of modules are included within the plurality) that can be configured for performing a multiplex detection of at least two protein analytes and/or 1, 2, 3, 4, 5, 6, 7, 8, 9, 10, 11, 12, 13, 14, or 15 modules (depending on whether other types of modules are included within the plurality) that can be configured for sequencing and detecting a nucleic acid molecule and/or 1, 2, 3, 4, 5, 6, 7, 8, 9, 10, 11, 12, 13, 14, or 15 modules (depending on whether other types of modules are included within the plurality) that can be configured for performing PCR and/or 1, 2, 3, 4, 5, 6, 7, 8, 9, 10, 11, 12, 13, 14, or 15 modules (depending on whether other types of modules are included within the plurality) that can be configured for performing flow cytometry and or cell capture.

Some embodiments of the invention relate to a method for operating a sample processing apparatus. In the method, a sample cartridge holding an unprepared sample at one of a plurality of sample preparation modules held by an enclosure can be received. Each sample preparation module can be configured to only perform sample preparation on a sample within a corresponding removable sample cartridge. The sample for a corresponding biological testing process can be prepared. At least one sample cartridge, holding the prepared sample, can be received at one of a plurality of sample processing modules held by the enclosure. Each sample processing module can be configured to perform at least one of a plurality of biological testing processes. The at least one biological testing process can then be performed on the prepared sample using the corresponding sample processing module.

In some embodiments, performing the at least one biological testing process can include sequencing a nucleic acid.

In some embodiments, performing the at least one biological testing process can include detecting a nucleic acid analyte.

In some embodiments, performing the at least one biological testing process can include detecting at least one protein analyte.

In some embodiments, performing the at least one biological testing process can include assessing a chromosomal copy number of at least one gene of interest.

In some embodiments, performing the at least one biological testing process can include performing a multiplex detection by hybridization to a detection array of at least two nucleic acid analytes.

In some embodiments, performing the at least one biological testing process can include performing a multiplex detection by hybridization to a detection array of at least two protein analytes.

In some embodiments, performing the at least one biological testing process further can include performing nucleic acid amplification and detection; and detecting at least one nucleic acid analyte.

In some embodiments, performing the at least one biological testing process further can include performing flow cytometry on a mixed population of cells in a sample.

In some embodiments, preparing the sample can include performing a sample processing protocol for isolation or purification of at least one nucleic acid.

In some embodiments, preparing the sample can include performing a sample processing protocol for isolation or purification of a particular cell type from the sample.

In some embodiments, at least one module can be configured for the isolation and/or purification of a particular cell type, for example a circulating tumor cell expressing a particular cell surface marker.

BRIEF DESCRIPTION OF THE DRAWINGS

FIG. 3B shows a method 318 for using a sample processing apparatus, according to some embodiments of the invention.

DETAILED DESCRIPTION OF THE INVENTION

Figure 1A:
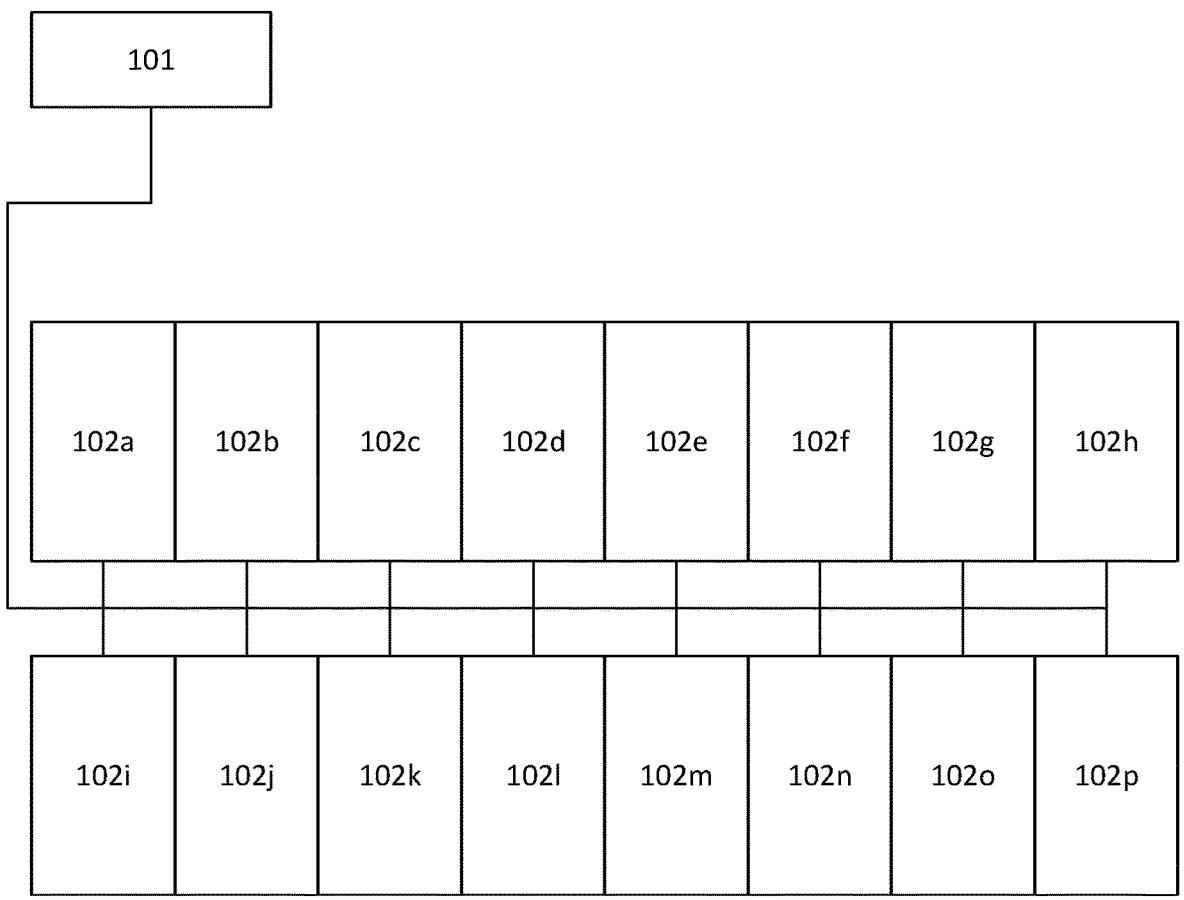
FIG. 1A shows a schematic diagram of a sample processing apparatus, according to some embodiments of the invention.

Embodiments of the invention relate to an apparatus for performing multiple types of assays and related sample preparation. The apparatus can include a heterogeneous testing module population, typically having, or is capable of having at least, 2-15 different types of modules. The modules can be configured for different types of assays (e.g., immunoassay, PCR, rapid PCR, sequencing, chromosomal analysis, and flow cytometry, etc.) for detecting different types of target analytes (e.g., nucleic acid, whole cell, DNA, RNA, protein, virus, drugs, etc.). The apparatus can also include modules dedicated to sample preparation (e.g., lysis, chemical treatment, filtration, etc.). A cartridge-based sample holder is standardized for each type of module, so that in most cases each module can interface with the same cartridge. The modules, regardless of type, can all share the same chassis footprint and electronic interface, such that types of modules can be changed with little difficulty.

As used herein, the term "biological sample" (interchangeable with "test sample" or "sample") encompasses any material that may contain an analyte of interest (e.g., a particular protein or nucleic acid), often taken from or otherwise derived from a living organism. "Biological samples" may include, but are not limited to, sections of tissues such as biopsy and autopsy samples, and frozen or paraffin embedded sections taken for histological or pathology purposes. Such samples may include whole blood, serum, plasma, cerebrospinal fluid, sputum, tissue, cultured cells, e.g., primary cultures, explants, transformed cells, stool, urine, vesicle fluid, mucus, and other bodily secretion, or tissue that could be sampled with a swab device. Furthermore, in some cases, a "biological sample" can be material taken from an environment (e.g., water, air, soil, and the like) where the presence of a particular organism may be suspected.

As used herein, the term "configured" describes a particular arrangement of hardware components, such as chassis, heaters, fans, optical sensors, fluid couplings, fluid passages, microfluidics, piezoelectric components, processor, memory containing instructions, supporting circuitry, and/or connectors, etc.

As used herein, the term "sample processing module" (interchangeable with "processing module" and "module") is defined as a modular sub-portion of a testing apparatus, which has a particular physical form factor compatible with the apparatus and includes hardware components (heaters, fans, optical sensors, fluid couplings, fluid passages, microfluidics, piezoelectric components, processor, memory containing instructions, supporting circuitry, and/or connectors, etc.) configured to perform a particular process for a sample.

As used herein, the term "sample preparation" is defined as a process typically performed prior to one or more particular assays. The process changes a physical characteristic of a sample prior to the assay(s), for example, by physical, chemical, and/or enzymatic treatment (e.g., lysis by sonification, enzymatic, detergents, solvents, cell-bomb, etc., filtration, and/or concentration).

As used herein, the term "sample preparation module" is defined as a subset of a sample processing module, and accordingly is of the same form factor, which is configured to only perform the preparation, e.g., isolation or concentration of one or more analyte of interest.

As used herein, the term "assay" (interchangeable with "testing process" and "biological testing process") is defined to be an investigative procedure performed on a sample, including but not limited to, determining the presence/absence and/or the quantity/concentration of a particular analyte.

Non-limiting exemplary analytes can include any nucleic acids and/or proteins, analytes specific for bacterial pathogens (e.g. methicillin resistant *Staphylococcus aureus, C. difficile*, tuberculosis, group B strep., *chlamydia*, and gonorrhea), viral pathogens (e.g. influenza, HIV, HCV, and HBV), tumor cells (e.g., bladder cancer, lung cancer, breast cancer, colon cancer, and leukemia), biothreat analytes such as anthrax or ricin, chromosomal alterations, such as gene duplication, gene deletions or gene translocations, cells expressing specific cell surface markers such as CD4+ cells, detection of gene mutation/alterations such as single nucleotide polymorphisms (SNPs) and methylation status of genes.

As used herein, the term "removable sample cartridge" (interchangeable with "sample cartridge" and "cartridge") refers to a specialized container for holding a sample that is configured to temporarily physically interface with a sample processing module such that control aspects (fluid connections, heaters, piezoelectric components, optical sensors, etc.) of the sample processing module can directly or indirectly perform a process on the sample within the container, after which the removable sample cartridge can be removed from the sample processing module to further analyze, process, or dispose of the sample. The removable sample cartridge couples and uncouples with the sample processing module without the need for using additional tools (e.g., screwdriver, hex-key, etc.) to fasten the removable sample cartridge to the sample processing module, akin to an electrical plug interfacing with an electrical wall outlet, except for cases of jamming or other malfunction, which may require such tools to help remove the cartridge. In some embodiments, the removable sample cartridge may contain, or has physical aspects for receiving, particular chemicals, such as primers and reagents (including reactants).

In this application, the term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, mutations including point mutations, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons).

A "polynucleotide hybridization method" as used herein refers to a method for detecting the presence and/or quantity of a polynucleotide based on its ability to form Watson-Crick base-pairing, under appropriate hybridization conditions, with a polynucleotide probe of a known sequence.

In this application, the terms "polypeptide," "peptide," and "protein" are used interchangeably to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, these terms encompass amino acid chains of any length, including full-length proteins (i.e., antigens), wherein the amino acid residues are linked by covalent peptide bonds. The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine.

As used herein, the terms "multiplex" and "array" refer to an assay format that permits simultaneous detection and/or quantification of multiple analytes (e.g., dozens or more of the same or different molecules) in a single run/cycle of the assay.

As used herein, the term "solid support" refers to an inert solid material, which may be a natural material, such as glass and collagen, or a synthetic material, such as acrylamide, cellulose, nitrocellulose, silicone rubber, polystyrene, polyethylene vinyl acetate, polypropylene, polymethacrylate, polyethylene, polysilicates, polyethylene oxide, polycarbonates, teflon, fluorocarbons, nylon, polyanhydrides, polyglycolic acid, polylactic acid, polyorthoesters, polypropylfumarate, glycosaminoglycans, and polyamino acids. One example is silica gel preimpregnated with fluorogenic substrates. A "solid support" typically provides a supporting structure for performing an assay in various apparatus of this application.

I. Sample Processing Apparatus with Heterogeneous Population of Modules

FIG. 1A shows a schematic diagram of a biological sample processing apparatus 100, according to some embodiments of the invention. The apparatus 100 includes a plurality of, generally at least two, processing modules 102*a-p*. The processing module population is heterogeneous in nature, and therefore the modules do not necessarily perform the same processing tasks. In some embodiments, the apparatus 100 can include sub-groups of identical processing modules. For example, processing modules 102*a-h* can each be PCR processing modules, processing modules 102*i-m* can be array modules, and processing modules 102*m-p* can be dedicated sample preparation modules (e.g., lysis by sonification, enzymatic, detergents, solvents, cell-bomb). In some embodiments, the apparatus 100 includes at least one dedicated sample preparation module, which can be configured to perform sample preparation for other processing modules that in turn can be configured only to perform assays on pre-processed biological samples.

The sample processing modules 102*a-p* are connected by a communications bus to a control unit 104. The control unit 104 is configured to independently operate each sample processing module 102*a-p*. The control unit 104 can be, for example, a general purpose or specific purpose computer. The control unit 104 generally includes at least one processor and supporting circuitry, and memory storing instructions for independently operating each sample processing module 102*a-p*. In some embodiments, the control unit 104 is structurally integrated into the apparatus 100. In other embodiments, the control unit 104 is remotely connected to the apparatus via a wired or wireless connection.

Figure 1B:
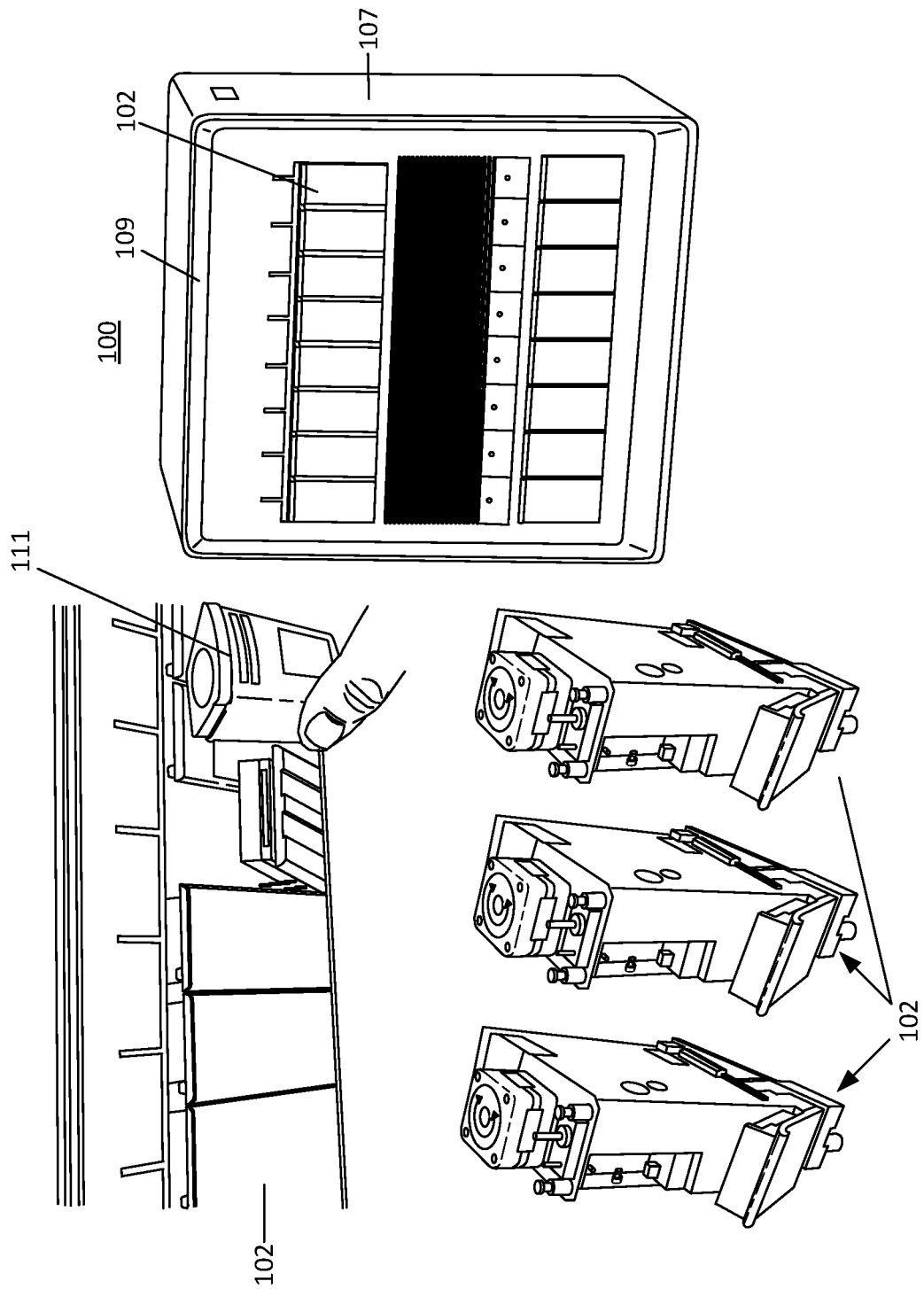
FIGS. 1B and 1C show various external and internal perspective views of a sample processing apparatus, according to some embodiments of the invention.

FIG. 1B shows a perspective view of the apparatus 100. In some embodiments, the apparatus 100 includes a housing/enclosure 107 configured to be semi-portable, such that it can be easily be used within a laboratory environment, akin to a desktop computer. As shown, the housing 107 can be rectangular in shape and have a front-facing interface panel 109 that provides user access to the plurality of processing modules 102*a-p*.

Generally, each sample processing module 102*a-p* will share the same structural format and can be configured to electronically interface with the enclosure via a shared type of connector. This arrangement allows for easy swapping of modules when different configuration needs arise for the user. Each sample processing modules 102*a-p* is configured to interface with a sample testing cartridge 111, for example, such as the vessel disclosed in FIG. 1 of commonly assigned U.S. Pat. No. 6,660,228, entitled "APPARATUS FOR PERFORMING HEAT-EXCHANGING, CHEMICAL REACTIONS, which is incorporated by reference, and also such as, for example, the vessel disclosed in FIG. 1 of commonly assigned U.S. Pat. No. 6,391,541, entitled "APPARATUS FOR ANALYZING A FLUID SAMPLE", which is incorporate by reference herein. Accordingly, in some embodiments, the same cartridge can be used within any of the sample processing modules 102*a-p*. Aspects of Int'l Pub. No. WO/2002/18902, entitled "FLUID METERING AND DISTRIBUTION SYSTEM", Int'l Pub. No. WO/2000/072970, entitled "CARTRIDGE FOR CONDUCTING A CHEMICAL REACTION", and Int'l Pub. No. WO/2000/073412, entitled "APPARATUS AND METHOD FOR ANALYZING A FLUID SAMPLE", can also be used within any of the sample processing modules. These references are incorporated by reference herein.

Figure 1C:
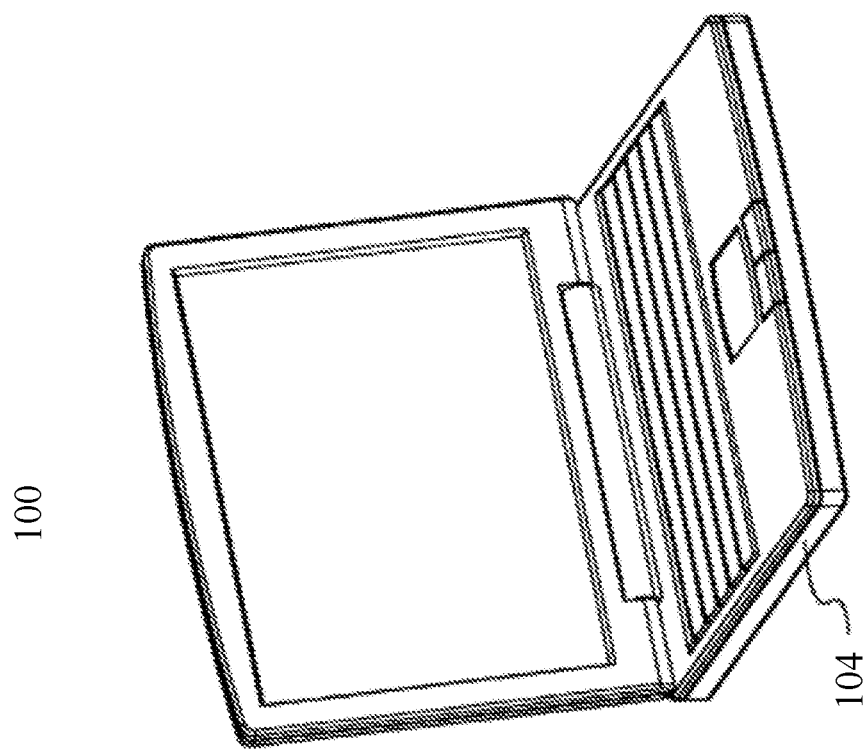
Figure 1C:
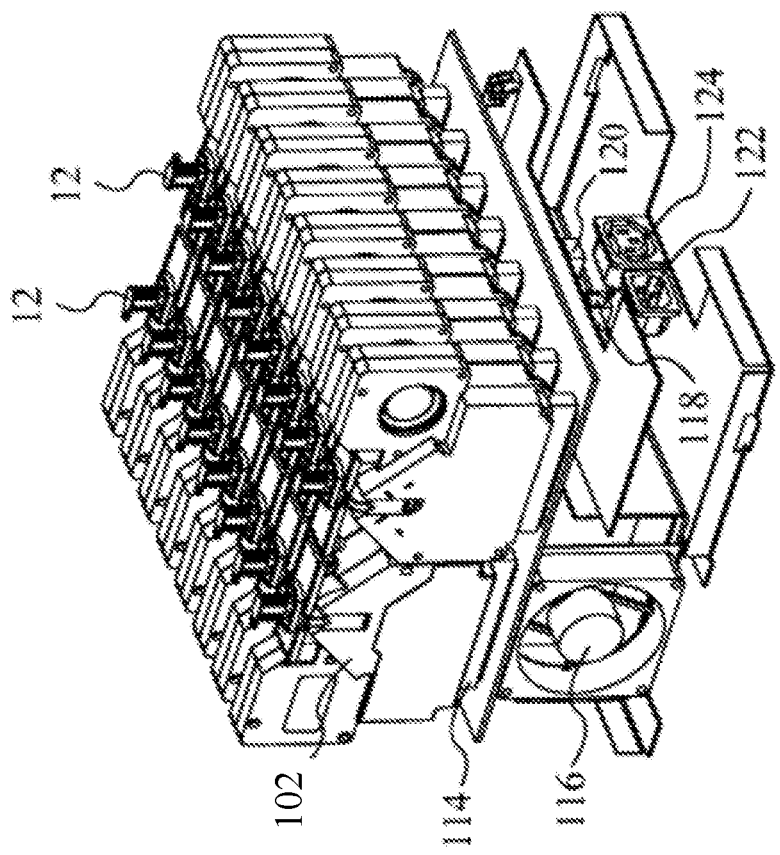
Figure 1D:
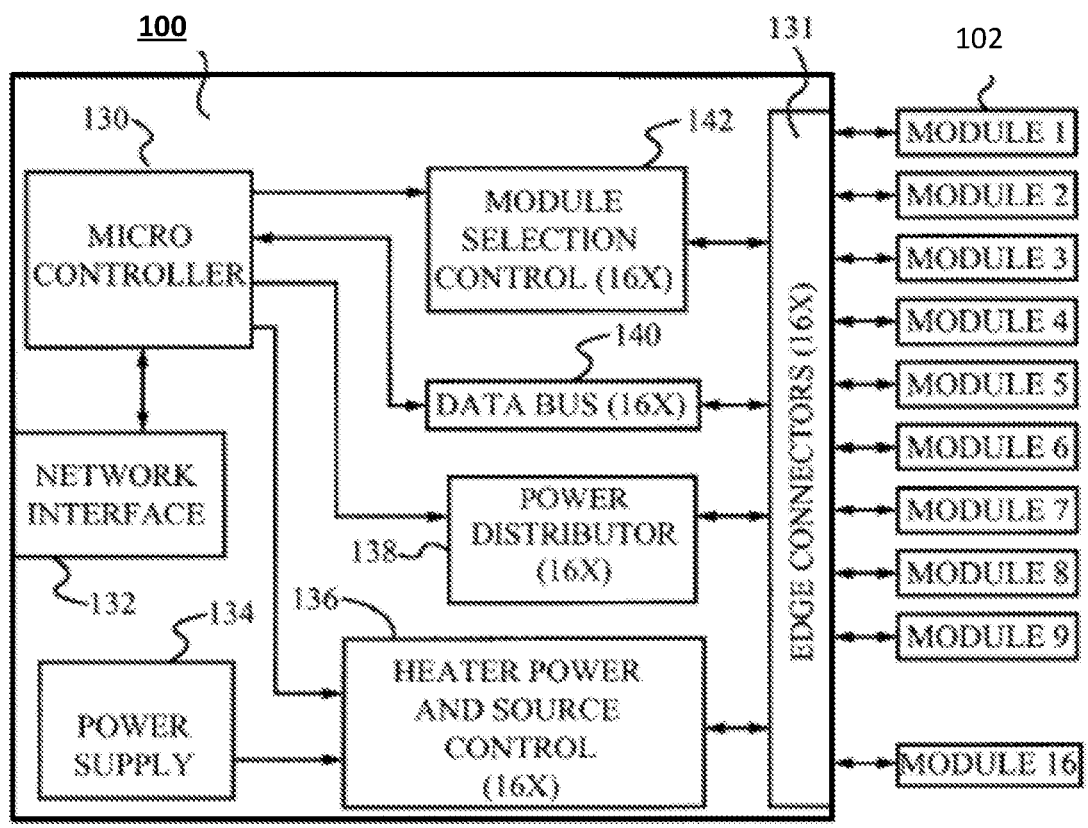
FIG. 1D is a schematic, block diagram of a sample processing apparatus, according to some embodiments of the invention.

FIG. 1C depicts the apparatus 100 according to some embodiments the present invention. The control unit 104 is depicted as personal computer. The apparatus 100 has a main logic board with edge connectors 114 for establishing electrical connections to the modules 102*a-p*. The apparatus 100 also preferably includes a fan 116 for cooling its electronic components. The apparatus 100 may be connected to the controller 112 using any suitable data connection, such as a universal serial bus (USB), ethernet connection, or serial line. It is presently preferred to use a USB that connects to the serial port of controller 112. Alternatively, the controller may be built into the apparatus 100.

The processing modules 102a-p are preferably independently controllable so that different chemical reactions and sample preparations can be run simultaneously in the apparatus 100. The apparatus 100 is preferably modular so that each processing module can be individually removed from the apparatus 100 for servicing, repair, or replacement. This modularity reduces downtime since all the processing modules 102a-p are not off line to repair one, and the instrument 100 can be upgraded and enlarged to add more modules as needed.

In embodiments in which the apparatus 100 operates on external power, e.g. 110V AC, the instrument preferably includes two power connections 122, 124. Power is received though the first connection 122 and output through the second connection 124. Similarly, the apparatus 100 preferably includes network interface inlet and outlet ports 118, 120 for receiving a data connection through inlet port 118 and outputting data to another apparatus through outlet port 120.

FIG. 1E is a schematic, block diagram of the apparatus 100, according to some embodiments of the invention. The apparatus 100 includes a power supply 134 for supplying power to the instrument and to each module 60. The power supply 134 may comprise an AC/DC converter for receiving power from an external source and converting it to direct current, e.g., for receiving 110V AC and converting it to 12V DC. Alternatively, the power supply 134 may comprise a battery, e.g., a 12V battery. The apparatus 100 also includes a microprocessor or microcontroller 130 containing firmware for controlling the operation of the apparatus 110 and modules 60. The microcontroller 130 communicates through a network interface 132 to the controller computer via, for example, a USB connector.

The apparatus 100 further includes a heater power source and control circuit 136, a power distributor 138, a data bus 140, and a module selection control circuit 142. Due to space limitations in patent drawings, control circuit 136, power distributor 138, data bus 140, and control circuit 142 are shown only once in the block diagram of FIG. 1E. However, the apparatus 100 may contain one set of these four functional components 136, 138, 140, 142 for each processing module 102. Thus, in the embodiment of FIG. 1E, the apparatus 100 includes sixteen control circuits 136, power distributors 138, data buses 140, and control circuits 142. Similarly, the apparatus 100 also includes edge connectors 131 for connecting to each of the processing modules 102, so that the instrument includes sixteen edge connectors for the embodiment shown in FIG. 1E. The edge connectors are preferably 120 pin card edge connectors that provide cableless connection from the apparatus 100 to each of the modules 60. Each control circuit 136, power distributor 138, data bus 140, and control circuit 142 is connected to a respective one of the edge connectors and to the microcontroller 130.

Each heater power and source control circuit 136 is a power regulator for regulating the amount of power supplied to the heating element(s) of a respective one of the modules 60. The source control circuit 136 is preferably a DC/DC converter that receives a +12V input from the power supply 134 and outputs a variable voltage between 0 and −24V. The voltage is varied in accordance with signals, received from the microcontroller 130. Each power distributor 138 provides −5 v, +5V, +12V, and GND to a respective module 60. The power distributor thus supplies power for the electronic components of the module. Each data bus 140 provides parallel and serial connections between the microcontroller 130 and the digital devices of a respective one of the modules 60. Each module selection controller 94 allows the microcontroller 130 to address an individual module 60 in order to read or write control or status information.

II. Module Configurations

Figure 2A:
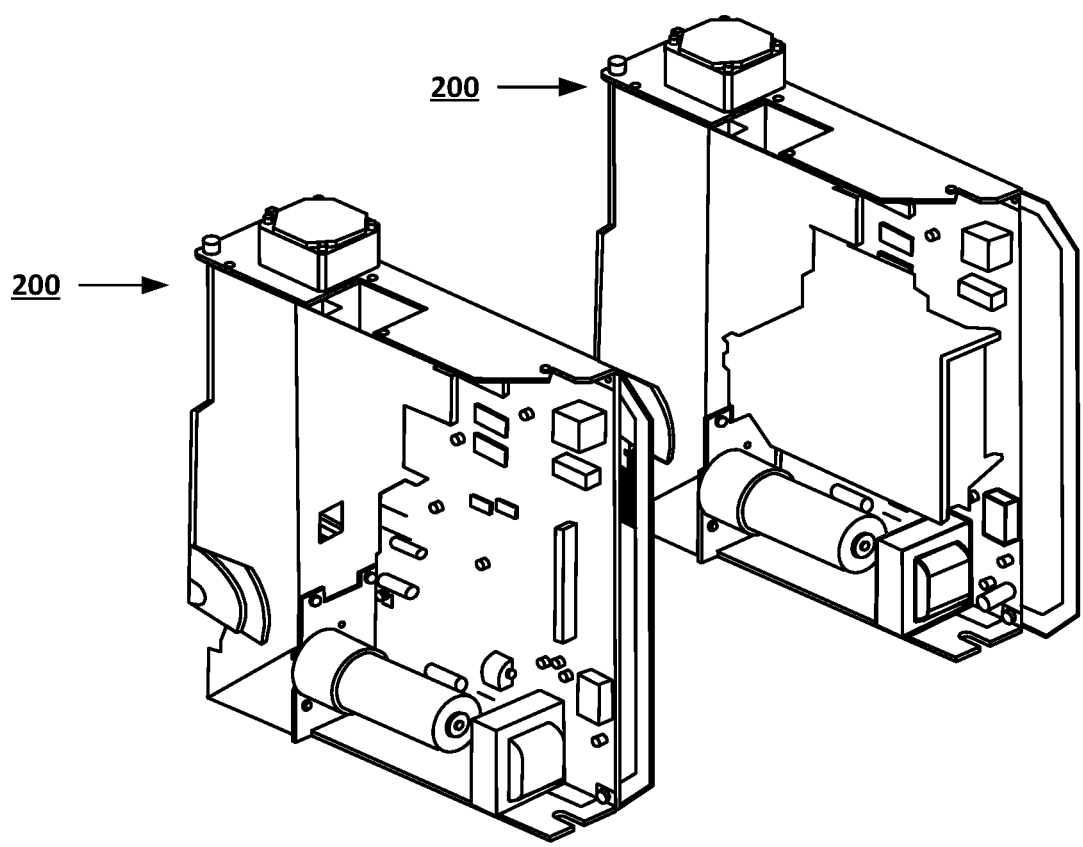
FIG. 2A shows a rear perspective view of sample processing modules, according to some embodiments of the invention.

FIG. 2A shows a rear perspective view of sample processing modules 200, according to some embodiments of the invention. Generally, the sample processing module 200 can be configured according to a variety of processing tasks using, for example, the shown form factor. This enables a user to customize and/or reconfigure modules with relative ease. In some embodiments, the apparatus 100 includes up to 15 different types of sample processing modules for performing assays, and at least one sample preparation module.

In some embodiments, the sample processing module 200 is configured as a sample preparation module to prepare a sample for later processing (e.g., lysis by ultrasonification). An example of such a configuration is shown in commonly assigned U.S. Pat. No. 6,739,537, entitled "APPARATUS AND METHOD FOR RAPID DISRUPTION OF CELLS OR VIRUSES", which is incorporated by reference. Another example of such a configuration is shown in commonly assigned U.S. Pub. No. US 2010/0129827, entitled "METHOD AND DEVICE FOR SAMPLE PREPARATION CONTROL", which is incorporated by reference.

The sample processing module 200 can be a dedicated module configured to only perform sample preparation, and thereby not include additional components (e.g., heat cycling components, optical sensors, etc.) required to perform a post-preparation assay. In some embodiments, such a sample preparation module can be configured to implement a sample preparation protocol for detection of a nucleic acid. In some embodiments, a sample preparation module can be configured to implement a sample preparation protocol for detection of a protein analyte. In some embodiments, a sample preparation module can be configured to chemically treat and/or filter a cell or a virus. In some embodiments, a sample preparation module can be configured to implement more than one type of sample processing protocol.

In some embodiments, flow cytometry is one of the detection methods that can be used in one or more sample processing modules for detecting the presence of a predetermined target, such as a certain cell type or a population of cells that express a particular marker. Methods and instrumentation for practicing flow cytometry are known in the art, and can be used in the practice of the present invention. Flow cytometry in general resides in the passage of a suspension of cells or microparticles comprising a label (e.g. a fluorophore) as a stream past a laser beam and the detection of the label (e.g. fluorescent emission) from each particle by a detector, such as a photo multiplier tube. Detailed descriptions of instrumentation and methods for flow cytometry are found in the literature. Examples are McHugh, "Flow Microsphere Immunoassay for the Quantitative and Simultaneous Detection of Multiple Soluble Analytes," *Methods in Cell Biology* 42, Part B (Academic Press, 1994); McHugh et al., "Microsphere-Based Fluorescence Immunoassays Using Flow Cytometry Instrumentation," *Clinical Flow Cytometry*, Bauer, K. D., et al., eds. (Baltimore, Maryland, USA: Williams and Williams, 1993), pp. 535-544; Lindmo et al., "Immunometric Assay Using Mixtures of Two Particle Types of Different Affinity," *J. Immunol. Meth.* 126: 183-189 (1990); McHugh, "Flow Cytometry and the Application of Microsphere-Based Fluorescence Immunoassays," *Immunochemica* 5: 116 (1991); Horan et al., "Fluid Phase Particle Fluorescence Analysis: Rheumatoid Factor Specificity Evaluated by Laser Flow Cytophotometry," *Immunoassays in the Clinical Laboratory,* 185-189 (Liss 1979); Wilson et al., "A New Microsphere-Based Immunofluorescence Assay Using Flow Cytometry," *J. Immunol. Meth.* 107: 225-230 (1988); Fulwyler et al., "Flow Microsphere Immunoassay for the Quantitative and Simultaneous Detection of Multiple Soluble Analytes," *Meth. Cell Biol.* 33: 613-629 (1990); Coulter Electronics Inc., United Kingdom Patent No. 1,561, 042 (published Feb. 13, 1980); and Steinkamp et al., *Review of Scientific Instruments* 44(9): 1301-1310 (1973). These references are incorporated herein by reference.

In some embodiments, one or more of the sample processing modules can be configured for detection of nucleic acids and/or proteins. Basic texts disclosing general methods and techniques for detection of nucleic acids and proteins include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994). These references are incorporated herein by reference. A variety of polynucleotide amplification methods are well established and frequently used in research. For instance, the general methods of polymerase chain reaction (PCR) for polynucleotide sequence amplification are well known in the art and are thus not described in detail herein. For a review of PCR methods, protocols, and principles in designing primers, see, e.g., Innis, et al., *PCR Protocols: A Guide to Methods and Applications,* Academic Press, Inc. N.Y., 1990, which is incorporated by reference herein. PCR reagents and protocols are also available from various commercial vendors.

Figure 2B:
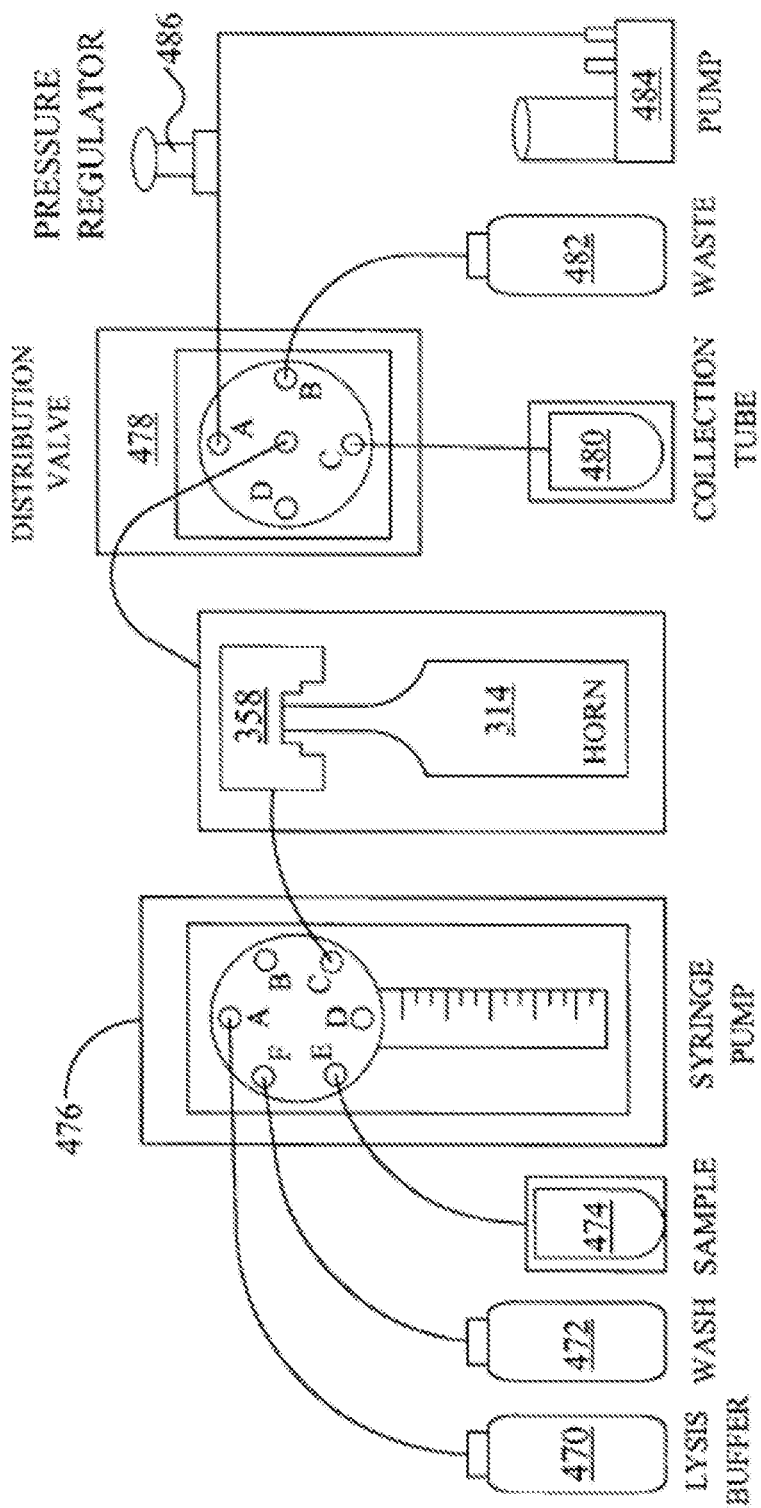
FIG. 2B is a schematic, block diagram of aspects of a sample processing apparatus interfacing with the sample processing module, according to some embodiments of the invention.

FIG. 2B is a schematic, block diagram of aspects of the apparatus 100 interfacing with the sample processing module 200, which is configured as a sample preparation module, according to some embodiments of the invention. The apparatus 100 can interface with a cartridge having a container 470 for holding lysis buffer, a container 472 containing wash solution, and a sample container 474 for holding a fluid sample. The containers 470, 472 and sample container 474 are connected via tubing to the valve ports of a syringe pump 476 of the apparatus 100. The inlet port of container 358 is also connected to the syringe pump 476. The outlet port of container 358 is connected to the common port of a distribution valve 478. The cartridge can also include a collection tube 480 for receiving intracellular material removed from the sample, a waste container 482 for receiving waste. The apparatus 100 can also include a pressure source, such as a pump 484. The collection tube 480, waste container 482, and pump 484 are connected to respective peripheral ports of the distribution valve 478. A pressure regulator 486 regulates the pressure supplied by the pump 484. The transducer 314 is preferably an ultrasonic horn for sonicating a fluid sample. In some embodiments, a sample can be sonicated for 10 to 40 seconds at a frequency in the range of 20 to 60 kHz. In some embodiments, a sample can be sonicated for 15 seconds at a frequency of 40 kHz. The amplitude of the horn tip can be in the range of 20 to 25 µm (measured peak to peak).

Figure 2C:
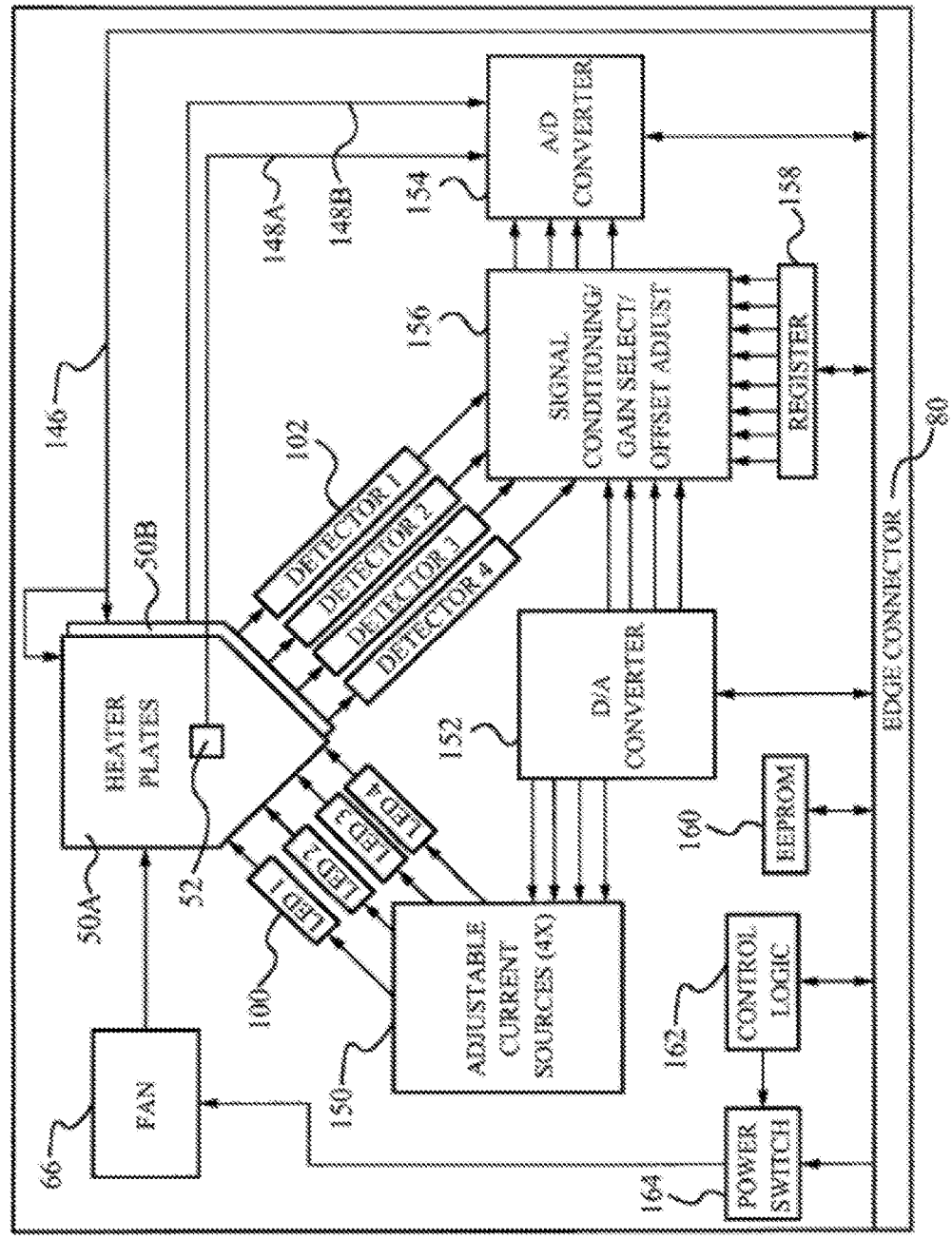
FIG. 2C is a schematic, block diagram of electronic components of a sample processing module, according to some embodiments of the invention.

FIG. 2C is a schematic, block diagram of the electronic components of the sample processing module 200 configured as a heat-exchanging module, as shown in the rightmost embodiment of FIG. 2A. Each sample processing module 200 includes an edge connector 80 for cableless connection to a corresponding edge connector of the apparatus. The sample processing module 200 also includes heater plates 50A, 50B each having a resistive heating element as described above. The plates 50A, 50B are wired in parallel to receive power input 146 from the apparatus. The plates 50A, 50B also include temperature sensors 52, e.g. thermistors, that output analog temperature signals to an analog-to-digital converter 154. The converter 154 converts the analog signals to digital signals and routes them to the microcontroller in the apparatus 100 through the edge connector 80. The heat-exchanging module also includes a cooling system, such as a fan 66, for cooling the plates 50A, 50B. The fan 66 receives power from the apparatus 100 and is activated by switching a power switch 164. The power switch 164 is in turn controlled by a control logic block 162 that receives control signals from the microcontroller in the apparatus.

The sample processing module 200 further includes at least four light sources, such as LEDs 100, for excitation of fluorescent labels in the reaction mixture and at least four detectors 102, preferably photodiodes, for detecting fluorescent emissions from the reaction mixture. The module also includes an adjustable current source 150 for supplying a variable amount of current (e.g., in the range of 0 to 30 mA) to each LED to vary the brightness of the LED. A digital-to-analog converter 152 is connected between the adjustable current source 150 and the microcontroller of the apparatus to permit the microcontroller to adjust the current source digitally. The adjustable current source 150 may be used to ensure that each LED has about the same brightness when activated. Due to manufacturing variances, many LEDs have different brightnesses when provided with the same amount of current. The brightness of each LED may be tested during manufacture of the heat-exchanging module and calibration data stored in a memory 160 of the module. The calibration data indicates the correct amount of current to provide to each LED. The microcontroller reads the calibration data from the memory 160 and controls the current source 150 accordingly. The microcontroller may also control the current source 150 to adjust the brightness of the LEDs 100 in response to optical feedback received from the detectors 102.

The sample processing module 200 additionally includes a signal conditioning/gain select/offset adjust block 156 comprised of amplifiers, switches, electronic filters, and a digital-to-analog converter. The block 156 adjusts the signals from the detectors 102 to increase gain, offset, and reduce noise. The microcontroller in the apparatus controls block 156 through a digital output register 158. The output register 158 receives data from the microcontroller and outputs control voltages to the block 156. The block 156 outputs the adjusted detector signals to the microcontroller through the analog-to-digital converter 154 and the edge connector 80. The module also includes the memory 160, preferably a serial EEPROM, for storing data specific to the module, such as calibration data for the LEDs 100, thermal plates 50A, 50B, and temperature sensors 52, as well as calibration data for a deconvolution algorithm described in detail below.

Referring again to FIG. 1C, the apparatus 100 may be configured for manual filling and pressurization of each reaction vessel 12 by a human operator. Manual use of the apparatus 100 is suitable for lower throughput embodiments.

In some embodiments, the sample processing module 200 is configured to perform an assay for nucleic acid amplification and detection. In such a configuration, however, the sample processing module 200 can be a dedicated module configured to only perform heat cycling and sensing required for nucleic acid amplification and detection, and accordingly not include additional components (e.g., ultrasonic transducer) required to perform sample preparation.

In some embodiments, the sample processing module 200 is configured to perform an assay for detection of a protein analyte. In such a configuration, however, the sample processing module 200 can be a dedicated module configured to only perform detection of a protein analyte, and accordingly not include additional components (e.g., ultrasonic transducer) required to perform sample preparation.

In some embodiments, the sample processing module 200 is configured to perform an assay for assessing a chromosomal nucleic acid copy number of a nucleic acid. In such a configuration, however, the sample processing module 200 can be a dedicated module configured to only assesses a chromosomal nucleic acid copy number of a nucleic acid, and accordingly not include additional components (e.g., ultrasonic transducer) required to perform sample preparation.

In some embodiments, the sample processing module 200 is configured to perform an assay for multiplex detection of one or more nucleic acid analytes. In such a configuration, however, the sample processing module 200 can be a dedicated module configured to only perform a multiplex detection of one or more nucleic acid analytes, and accordingly not include additional components (e.g., ultrasonic transducer) required to perform sample preparation.

In some embodiments, the sample processing module 200 is configured to perform an assay for multiplex detection of one or more protein analytes. In such a configuration, however, the sample processing module 200 can be a dedicated module configured to only perform a multiplex detection of one or more protein analytes, and accordingly not include additional components (e.g., ultrasonic transducer) required to perform sample preparation.

In some embodiments, the sample processing module 200 is configured to perform an assay for sequencing and detecting a nucleic acid molecule. In such a configuration, however, the sample processing module 200 can be a dedicated module configured to only perform a sequencing and detecting a nucleic acid molecule, and accordingly not include additional components (e.g., ultrasonic transducer) required to perform sample preparation.

III. Methods of Sample Preparation

Figure 3A:
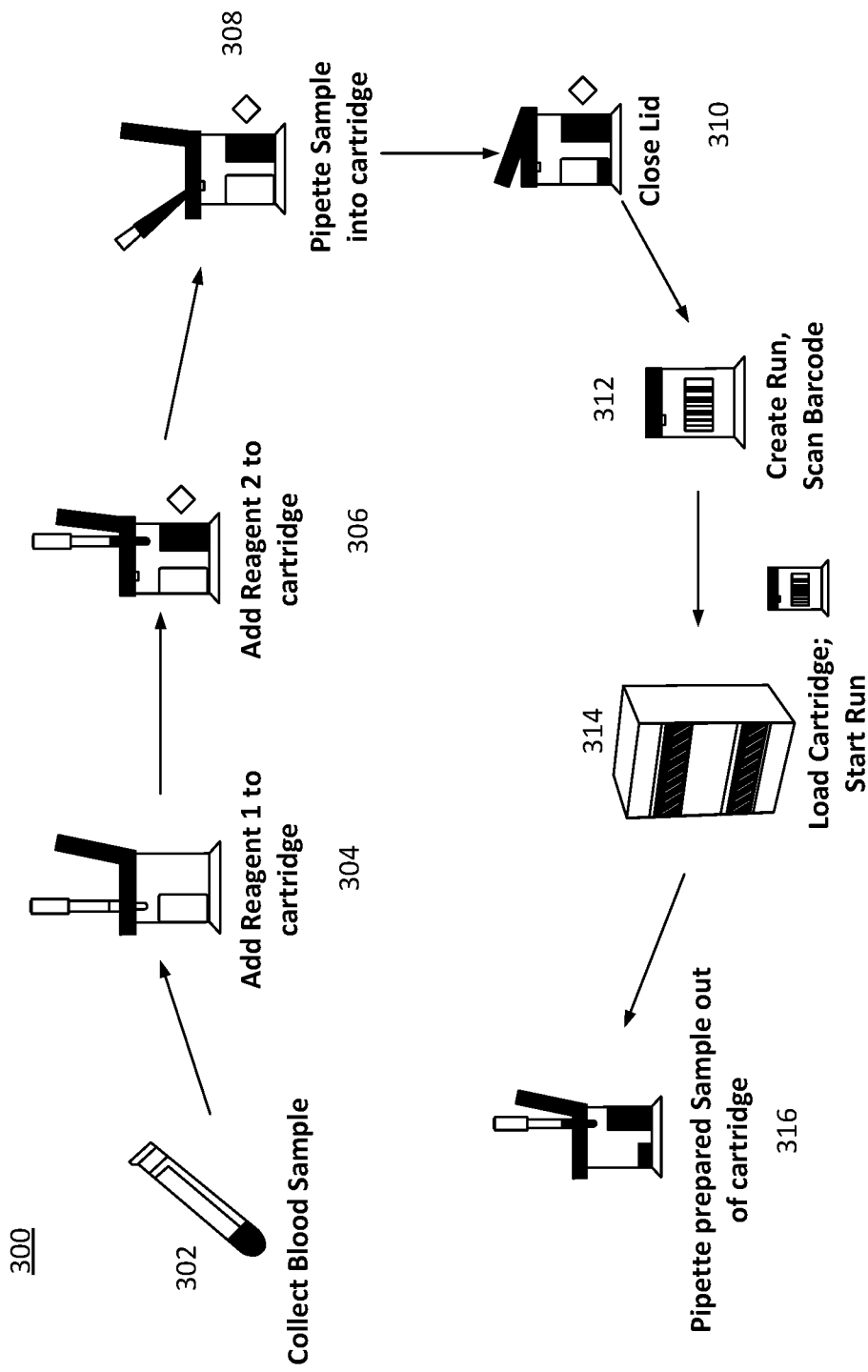
FIGS. 3A and 3B show flow chart illustrating various methods for using a sample processing apparatus, according to some embodiments of the invention.

FIG. 3A shows a flow chart illustrating a method 300 for using a sample processing apparatus, such as apparatus 100 of FIG. 1A. At operation 302, a sample, such as blood, is obtained. At operation 304, a first reagent is added to a sample preparation cartridge. At operation 306, a second reagent is added to the sample preparation cartridge. At operation 308 the sample is added to the sample preparation cartridge using, for example, a pipette, and the cartridge is closed at operation 310. At operation 312 a sample preparation protocol is readied by configuring the sample processing apparatus, and an associated barcode is created for tracking the cartridge. At operation 314, the cartridge is inserted into a sample processing module of the apparatus, and the apparatus is operated to start the sample preparation protocol. At operation 316, the sample preparation protocol is completed and the cartridge removed to pipette out the prepared sample.

Figure 3B:
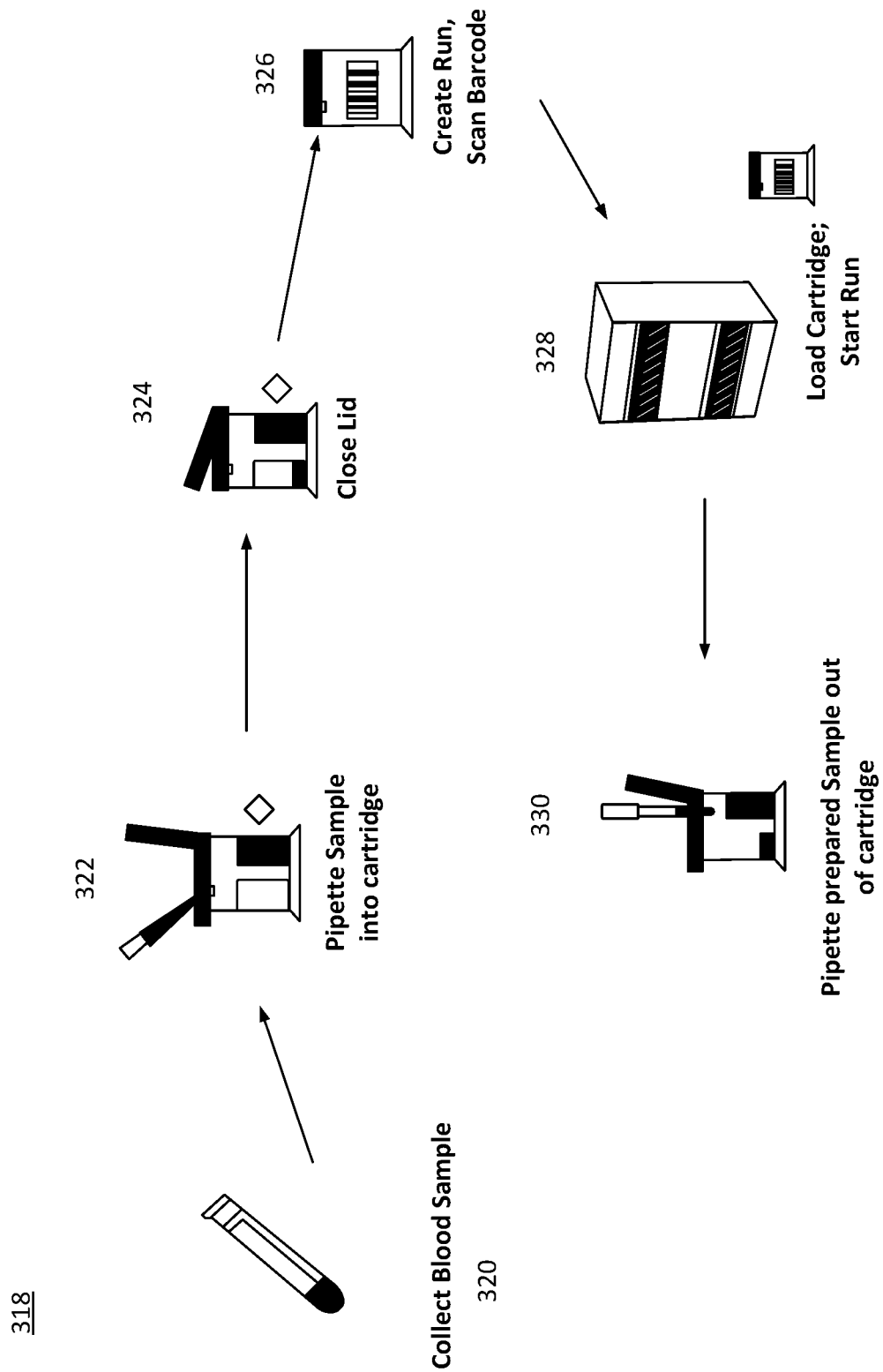

FIG. 3B shows a method 318 for using a sample processing apparatus, such as apparatus 100 of FIG. 1A. At operation 320, a sample, such as blood, is obtained. In the method 318, reagents do not need to be added to a sample preparation cartridge, since in some embodiments, the sample preparation cartridge comes with required reagents, or no additional reagents are required. At operation 322 the sample is added to a sample preparation cartridge using, for example, a pipette, and the cartridge is closed at operation 324. At operation 326 a sample preparation protocol is readied by configuring the sample processing apparatus, and an associated barcode is created for tracking the cartridge. At operation 328, the cartridge is inserted into a sample processing module of the apparatus, and the apparatus is operated to start the sample preparation protocol. At operation 330, the sample preparation protocol is completed and the cartridge removed to pipette out the prepared sample.

Following method 300 or method 318, a sample preparation all or a portion of the prepared sample can be added to one or more processing cartridges. Following this, the apparatus can be readied to implement one or more processes, such as any of the processes disclosed herein. The processing cartridges can then be inserted into respective sample processing modules and the apparatus operated to implement specific processes to those cartridges. The apparatus accordingly performs the processes and collects associated data. Alternatively, the cartridge used for sample preparation can also be used for performing an assay, thus making transfer of the prepared sample unnecessary.

Figure 4:
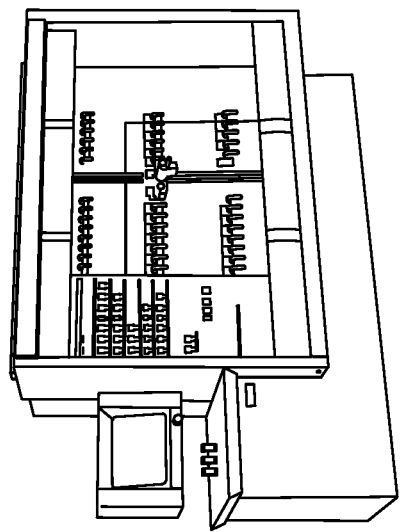
FIG. 4 shows various external configurations of sample processing apparatuses, according to some embodiments of the invention.
Figure 4:
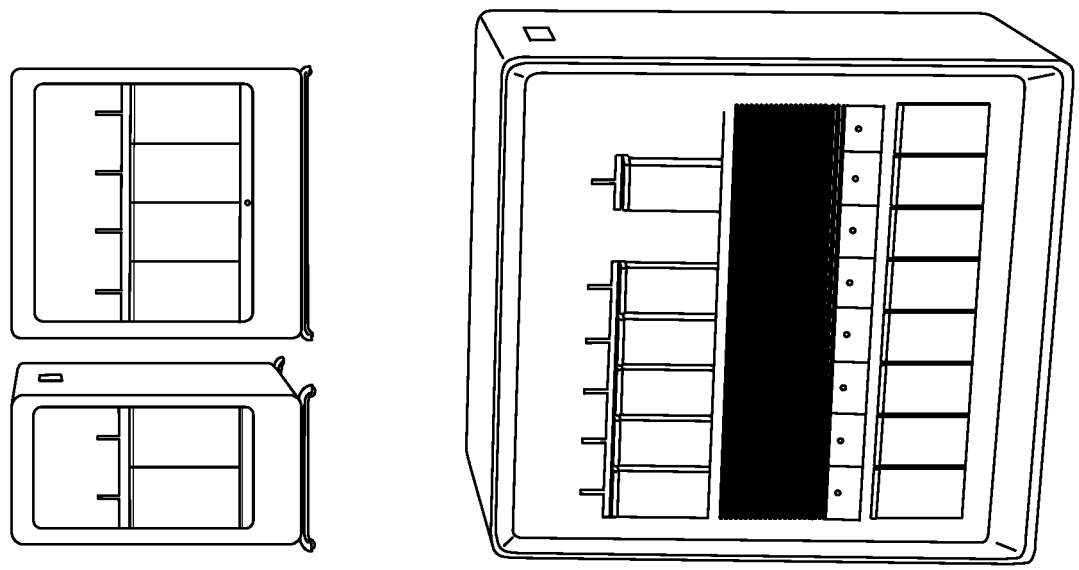

FIG. 4 shows embodiments of the sample processing apparatus can have varying amounts of sample processing modules. In some embodiments, the apparatus can have 2, 4, 16, 24, 32, 40, 48, or 80 sample processing modules. However, the invention is not limited to those examples, and different amounts of modules can also be employed.

Although the above description contains many specificities, these should not be construed as limitations on the scope of the invention, but merely as illustrations of some of the presently preferred embodiments. Many possible variations and modifications to the invention will be apparent to one skilled in the art upon consideration of this disclosure.

What is claimed is:

1. A method for operating a sample processing apparatus having an enclosure holding a plurality of sample processing modules and a sample preparation module, wherein each of the plurality of modules are removable and independently operable from each other module of the plurality, the method comprising:

receiving a sample cartridge holding an unprepared sample in the sample preparation module of the apparatus, the sample preparation module being configured to only perform sample preparation on a single sample at a time within a corresponding removable sample cartridge when accommodated therein, the sample cartridge containing one or more reagents required for sample preparation;

preparing the sample for a corresponding biological testing process within the sample cartridge using the sample preparation module in which the sample cartridge was received;

receiving the sample cartridge, holding the prepared sample having been prepared in the sample preparation module, in one of the plurality of sample processing modules of the apparatus, each sample processing module being configured to perform sample preparation on an unprepared sample in a given removable sample cartridge when accommodated therein, the sample cartridge containing the one or more reagents required for sample preparation, and each sample processing module configured to perform at least one of a plurality of biological testing processes on a single prepared sample in a given removable sample cartridge when accommodated therein; and performing the at least one biological testing process on the prepared sample within the sample cartridge using the corresponding sample processing module in which the sample cartridge was received.

2. The method of claim 1, wherein performing the at least one biological testing process comprises sequencing a nucleic acid.

3. The method of claim 1, wherein performing the at least one biological testing process comprises detecting a nucleic acid analyte.

4. The method of claim 1, wherein performing the at least one biological testing process comprises detecting at least one protein analyte.

5. The method of claim 1, wherein performing the at least one biological testing process comprises assessing a chromosomal nucleic acid copy number of at least one nucleic acid.

6. The method of claim 1, wherein performing the at least one biological testing process comprises performing a multiplex detection by hybridization to a detection array of at least two nucleic acid analytes.

7. The method of claim 1, wherein performing the at least one biological testing process comprises performing a multiplex detection by hybridization to a detection array of at least two protein analytes.

8. The method of claim 1, wherein performing the at least one biological testing process comprises performing nucleic acid amplification and detection; and detecting at least one nucleic acid analyte.

9. The method of claim 1, wherein preparing the sample comprises performing a sample processing protocol for at least one nucleic acid.

10. The method of claim 1, wherein performing the at least one biological testing process comprises hybridizing a nucleic acid to an array on a solid support.

\* \* \* \* \*